US007291502B2

(12) United States Patent
Franco

(10) Patent No.: US 7,291,502 B2
(45) Date of Patent: Nov. 6, 2007

(54) METHOD FOR PERFORMING A NON-INVASIVE BLOOD GAS TEST

(76) Inventor: Wayne P. Franco, 500 Cold Spring Rd., No. E217, Rocky Hill, CT (US) 06067

( * ) Notice: Subject to any disclaimer, the term of this patent is extended or adjusted under 35 U.S.C. 154(b) by 0 days.

(21) Appl. No.: 11/375,905

(22) Filed: Mar. 15, 2006

(65) Prior Publication Data

US 2007/0218559 A1   Sep. 20, 2007

(51) Int. Cl.
  *G01N 33/50* (2006.01)
(52) U.S. Cl. .......................... 436/68; 436/63; 436/163; 600/364
(58) Field of Classification Search ................ 436/63, 436/68, 163; 600/364; 702/19
  See application file for complete search history.

(56) References Cited

U.S. PATENT DOCUMENTS

| | | | |
|---|---|---|---|
| 3,224,436 A | 12/1965 | Massena | 600/361 |
| 3,638,109 A | 1/1972 | Harnoncourt | 324/438 |
| 3,874,850 A | 4/1975 | Sorensen et al. | 436/50 |
| 4,109,505 A | 8/1978 | Clark et al. | 73/1.02 |
| 4,114,604 A | 9/1978 | Shaw et al. | 600/399 |
| 4,163,734 A | 8/1979 | Sorensen et al. | 436/11 |
| 4,321,545 A | 3/1982 | Cameron | 324/442 |
| 4,353,867 A | 10/1982 | Luzzana | 204/403.14 |
| 4,493,692 A | 1/1985 | Reed | 604/6.14 |
| 4,512,348 A | 4/1985 | Uchigaki et al. | 600/364 |
| 4,786,394 A | 11/1988 | Enzer et al. | 204/401 |
| 5,061,631 A | 10/1991 | Calabrese | 436/11 |
| 5,526,809 A | 6/1996 | Fiddian-Green | 600/364 |
| 5,533,512 A | 7/1996 | Novotny et al. | 600/532 |
| 5,577,499 A | 11/1996 | Teves | 600/368 |
| 5,603,817 A | 2/1997 | Settler et al. | 204/433 |
| 5,630,413 A * | 5/1997 | Thomas et al. | 600/310 |
| 5,788,631 A | 8/1998 | Fiddian-Green | 600/309 |
| 5,800,361 A * | 9/1998 | Rayburn | 600/532 |
| 5,976,085 A | 11/1999 | Kimball et al. | 600/309 |
| 5,978,691 A * | 11/1999 | Mills | 600/334 |
| 6,096,275 A | 8/2000 | Greenberg | 422/82.02 |
| 2002/0087057 A1 | 7/2002 | Lovejoy et al. | 600/349 |
| 2003/0000833 A1 | 1/2003 | Mansouri et al. | 204/402 |
| 2003/0060727 A1 | 3/2003 | Kline | 600/538 |
| 2006/0105319 A1 * | 5/2006 | Rees et al. | 435/4 |

FOREIGN PATENT DOCUMENTS

| | | |
|---|---|---|
| IT | 1233172 | 3/1992 |
| JP | 08-182665 | 7/1997 |
| JP | 11056824 | 3/1999 |
| RU | 2105980 | 2/1998 |
| WO | WO9001896 A1 | 3/1990 |
| WO | WO 9806332 | 2/1998 |
| WO | WO 03063697 A1 | 8/2003 |

OTHER PUBLICATIONS

Rees et al. Computer Methods and Programs in Biomedicine, vol. 81, Jan. 2006, pp. 18-25.*
*The Accuracy of Calculated Base Excess in blood*, Lang, Clin Chem Lab Med. Apr. 2002; 40(4):404-10.
*The Van Slyke Equation*, Siggaard-Anderson, Scand J Clin Lab Invest Suppl. Jan. 1997; 37(146):15-20.
*Simultaneous Measurements of Blood pH, pCO2, pO2, and Concentrations of Hemoglobin and its Derivatives—A Muticenter Study*, Kokholm, Scand J Clin Lab Invest Suppl. 1990; 203:75-86.
*A Proposal for Analysing the Acid-Base Balance at Steady State in Vivo*, Mochizuki, Adv Exp Med Biol. 1998; 454:29-34.

* cited by examiner

*Primary Examiner*—Maureen M. Wallenhorst
(74) *Attorney, Agent, or Firm*—Ernest D. Buff & Associates, LLC; Ernest D. Buff; Theodore J. Piersou

(57) ABSTRACT

A non-invasive blood gas test is carried out by a method that utilizes a venous blood sample together with a pulse oximeter and a plurality of mathematical equations. The method generates the following data points of the blood: (i) the pH level; (ii) the [H+] concentration; (iii) the [$HCO_3-$] concentration; (iv) the partial pressure of carbon dioxide; and (v) the oxygen saturation level. Mathematical formulas, tables, and chemical equations provide a simple method by which a doctor or other medical professional can easily calculate the blood gas data without the need for an arterial blood sample or specialized machines. Blood gas measurements are obtained from a patient in a faster, safer and less painful manner than tests that require an arterial blood sample. In another embodiment of the present invention, a system for locating a dysfunctional organ in a patient is disclosed.

6 Claims, No Drawings

METHOD FOR PERFORMING A NON-INVASIVE BLOOD GAS TEST

BACKGROUND OF THE INVENTION

1. Field of the Invention

The present invention relates to a method for performing a non-invasive blood gas test, and more particularly to a blood gas testing method that utilizes a venous blood sample together with a pulse oximeter and a plurality of mathematical equations.

2. Description of the Prior Art

A blood gas test measures the amounts of oxygen and carbon dioxide in the blood and determines the acidity of the blood. This test is also commonly known as arterial blood gas analysis. Unlike most other blood tests, for which samples are drawn from a vein, the blood gases sample is taken from an artery, usually in the wrist, groin, or arm. The site is cleaned and disinfected; then a local anesthetic is injected. Once the area is numb, a needle is inserted into the artery and a sample of blood withdrawn into a special syringe that prevents contamination by outside air. After the sample is drawn, pressure must be applied to the site for 5 to 15 minutes to prevent bleeding. Blood gas measurements, performed by trained personnel, are usually carried out in a hospital, emergency room, or large laboratory setting. The analysis must be done immediately following sample collection; and specialized equipment is required.

Prior art teachings have disclosed various methods and techniques for acquiring blood gas data, or have related to blood gases more generally. Such examples can be found at: U.S. Pat. Nos. 3,224,436; 3,638,109; 3,874,850; 4,109,505; 4,114,604; 4,163,734; 4,321,545; 4,353,867; 4,493,692; 4,512,348; 4,786,394; 5,061,631; 5,526,809; 5,533,512; 5,577,499; 5,603,817; 5,788,631; 5,976,085; and 6,096,275; U.S. Pat. Publication Nos. 2002/0087057; 2003/0000833; and 2003/0060727; Foreign Patent Publication Nos. IT 1233172; JP 08182665; JP 11056824; RU 2105980; WO 03063697; WO 9001896; and WO 9806332; and the following scientific articles "The accuracy of calculated base excess in blood" at Clin Chem Lab Med. 2002 April; 40(4):404-10; "The van Slyke equation" at Scand J Clin Lab Invest Suppl. 1977 January; 37(146):15-20; "Simultaneous measurements of blood pH, pCO2, pO2 and concentrations of hemoglobin and its derivatives—a multicenter study" at Scand J Clin Lab Invest Suppl. 1990; 203:75-86; "A proposal for analyzing the acid-base balance at steady state in vivo" at Adv Exp Med Biol. 1998; 454:29-34; and Chemical Principles, 6th edition 1985 by CBS College Publishing. 1981. However, none of these references disclose or suggest a method for performing a non-invasive blood gas test that utilizes a venous blood sample together with a pulse oximeter, and a few specific mathematical equations (as disclosed hereinbelow) to safely determine the following data points of the blood sample: (i) the pH level; (ii) the [H+] concentration; (iii) the [$HCO_3$—] concentration; (iv) the partial pressure of carbon dioxide; and (v) the oxygen saturation level.

Because the blood sample is taken from the artery, a patient undergoing a traditional arterial blood gas test experiences more pain and discomfort than other blood tests that instead utilize venous blood samples. There remains a need in the art for a method for performing a non-invasive blood gas test. In particular, there remains a need in the art for a method for performing a non-invasive blood gas test that (i) does not require an arterial blood sample, but instead uses a venous blood sample; (ii) does not require the use of special machines to analyze a blood sample to give the gas levels of the blood; (iii) is less painful to the patient; (iv) is safe for the patient; and (v) generates fast results.

SUMMARY OF THE INVENTION

The present invention comprises a method for performing a non-invasive blood gas test. (As used herein the phrase "non-invasive" refers to a procedure wherein a blood sample is taken from the vein, not the artery). The method produces the following data points from the blood sample: (i) the pH level; (ii) the [H+] concentration; (iii) the [$HCO_3$—] concentration; (iv) the partial pressure of carbon dioxide; and (v) the oxygen saturation level. The salient features of the present invention comprise the following method steps: (i) measuring the pH level of the patient's venous blood; (ii) calculating the level of [H+] concentration (represented in mol per liter) in the patient's venous blood from the following formulas:

$$pH = -\log_{10}[H+]$$

$$[H+] = \text{Antilog}_{10}(-pH)$$

(iii) measuring the level of serum bicarbonate concentration, [$HCO_3$—] (in mEq/liter) in the patient's venous blood; (iv) calculating the partial pressure (in mm Hg) of carbon dioxide in the patient's venous blood from the following formula:

$$PCO_2 = [H+] \times (1/24) \times [HCO_3\text{—}],$$

wherein [H+] is represented in nmol/L;

and (v) determining the oxygen saturation level ($SO_2$) of the patient's arterial blood by using a pulse oximeter.

In an alternative embodiment of the present invention, in step (ii) of the present method, the [H+] concentration of the blood can be calculated from the pH value by using the following table:

| pH  | [H+] in nmol/L |
|-----|----------------|
| 6.8 | 160            |
| 6.9 | 125            |
| 7.0 | 100            |
| 7.1 | 80             |
| 7.2 | 63             |
| 7.3 | 50             |
| 7.4 | 40             |
| 7.5 | 32             |
| 7.6 | 26             |
| 7.7 | 20             |
| 7.8 | 16             |

Intermediate values falling within the given increments in the table can be calculated by mathematical extrapolation.

In another aspect of the present invention, a system for locating a dysfunctional organ in a patient is disclosed, the system comprising: (i) means for monitoring the pH level of the patient's venous blood; (ii) means for monitoring the complete metabolic profile of the patient; and (iii) computer programming means for processing the pH level data and the metabolic profile data in order to locate the dysfunctional organ in the patient.

Advantageously, in accordance with the present invention a non-invasive blood gas test can be carried out with fewer procedural steps in an accurate and reliable manner. Significantly, such testing is accomplished in much less time, with greater ease and at less expense. Blood gas tests carried out in accordance with the invention are particularly advantageous in that such tests (i) do not require an arterial blood sample, but instead use a venous blood sample; (ii) do not require the use of special machines to analyze a blood sample to give the gas levels of the blood; (iii) are less painful to the patient; (iv) are safe for the patient; and (v) generate fast results. During a terrorist attack, this would be the first response system to aid in the diagnosis and treatment of respiratory disorders, acid-base disorders, and to help locate any dysfunctional organs. The system could readily be adapted for use in the field. It would be possible to have a portable small pH and bicarbonate ($HCO_3-$) meter by fingerstick—similar to a glucometer. Thus, by simple calculations one could have a result at the bedside or in the field.

DETAILED DESCRIPTION OF THE INVENTION

Generally stated, the invention provides a method for performing a non-invasive blood gas test, and more particularly to a blood gas test that utilizes a venous blood sample together with a pulse oximeter and a few mathematical equations, as set forth herein. Typical data points that are collected during a blood gas test include measurements specific to the arterial blood. Arterial blood is oxygenated blood, found in the pulmonary veins, the left chambers of the heart, and the systemic arteries; it is bright red in color. Venous blood, on the other hand, is deoxygenated blood, found in the systemic veins, the right chambers of the heart, and the pulmonary arteries; it is dark red in color. Typical data points sought by a blood gas test include: (i) the pH level; (ii) the [H+] concentration; (iii) the [$HCO_3-$] concentration; (iv) the partial pressure of carbon dioxide; and (v) the oxygen saturation level. The only major difference between the chemistry of arterial blood and venous blood is the oxygen levels. Because the pH level; the [H+] concentration; the [$HCO_3-$] concentration; and the partial pressure of carbon dioxide are nearly the same as between arterial and venous blood, respectively, most data points for arterial blood can be gathered indirectly by analyzing the venous blood instead.

The present invention provides a fast, safe, and less painful method for obtaining blood gas measurements from a patient. The present method utilizes a venous blood sample along with a pulse oximeter to obtain blood gas measurements. Traditional blood gas analysis involves the collection of an arterial blood sample and the use of specialized machinery to generate the data points. An arterial needle stick is more painful than a venous needle stick because the needle must be inserted deeper beneath the skin of the patient in order to collect an arterial blood sample.

The present invention uses a pulse oximeter of the type commonly known in the art. An oximeter is a photoelectric device that is used for determining the oxygen saturation of the blood, and is completely non-invasive. A pulse oximeter is a special type of oximeter that measures the oxygen saturation of arterial blood by passing a beam of read and infrared light through a pulsating capillary bed, the ratio of red to infrared transmission varying with the oxygen saturation of the blood. Because it responds only to pulsatile objects, a pulse oximeter does not detect nonpulsating objects like skin and venous blood.

A blood gas test measures the amounts of oxygen and carbon dioxide in the blood and determines the acidity of the blood. It is also commonly known as arterial blood gas analysis. Unlike most other blood tests, for which samples are drawn from a vein, the blood gases sample is taken from an artery, usually in the wrist, groin, or arm. The site is cleaned and disinfected; then a local anesthetic is injected. Once the area is numb, a needle is inserted into the artery and a sample of blood withdrawn into a special syringe that prevents contamination by outside air. After the sample is drawn, pressure must be applied to the site for 5 to 15 minutes to prevent bleeding. Blood gas measurements, performed by trained personnel, are usually carried out in a hospital, emergency room, or large laboratory setting. The analysis must be done immediately following sample collection; and specialized equipment is required.

Measurement of blood gases is useful for evaluating diseases that affect breathing, such as pneumonia, chronic obstructive pulmonary disease, and tuberculosis. A blood gas measurement also provides information about the effectiveness of oxygen therapy. Information about the acidity of the blood provides a measure of kidney function and information that can be used to assess the body's metabolism. Common diseases requiring the use of a blood gas test are: diabetes, renal failure, heart failure, emphysema, metabolic alkalosis, metabolic acidosis, respiratory alkalosis, and respiratory acidosis.

Respiratory acidosis is characterized by a lower pH and an increased $PCO_2$, and is due to respiratory depression (not enough oxygen in and $CO_2$ out). This can be caused by many things, including pneumonia, chronic obstructive pulmonary disease (COPD), and over-sedation from narcotics. Respiratory alkalosis, characterized by a raised pH and a decreased $PCO_2$, is due to over ventilation caused by hyperventilating, pain, emotional distress, or certain lung diseases that interfere with oxygen exchange.

Metabolic acidosis is characterized by a lower pH and decreased $HCO_3-$; the blood is too acidic on a metabolic/kidney level. Causes include diabetes, shock, and renal failure. Metabolic alkalosis is characterized by an elevated pH and increased $HCO_3-$ and is seen in hypokalemia (low blood potassium), chronic vomiting (losing acid from the stomach), and sodium bicarbonate overdose.

The present invention comprises a method for performing a non-invasive blood gas test. (As used herein the phrase "non-invasive" refers to a procedure wherein a blood sample is taken from the vein, not the artery). The salient features of the present invention comprise the following method steps: (i) measuring the pH level of the patient's venous blood; (ii) calculating the level of [H+] concentration (represented in mol per liter) in the patient's venous blood from the following formulas:

$$pH = -\log_{10}[H+]$$

$$[H+] = \text{Antilog}_{10}(-pH)$$

(iii) measuring the level of serum bicarbonate concentration, [$HCO_3-$] (in mEq/liter) in the patient's venous blood; (iv) calculating the partial pressure (in mm Hg) of carbon dioxide in the patient's venous blood from the following formula:

$$PCO_2 = [H+] \times (1/24) \times [HCO_3-],$$

wherein [H+] is represented in nmol/L;

and (v) determining the oxygen saturation level ($SO_2$) of the patient's arterial blood by using a pulse oximeter.

In an alternative embodiment of the present invention, in step (ii) of the present method, the [H+] concentration of the blood can be calculated from the pH value by using the following table:

| pH | [H+] in nmol/L |
|---|---|
| 6.8 | 160 |
| 6.9 | 125 |
| 7.0 | 100 |
| 7.1 | 80 |
| 7.2 | 63 |
| 7.3 | 50 |
| 7.4 | 40 |
| 7.5 | 32 |
| 7.6 | 26 |
| 7.7 | 20 |
| 7.8 | 16 |

Intermediate values falling within the given increments in the table can be calculated by mathematical extrapolation.

The mathematical formulas and tables, and chemical equations, disclosed herein provide a simple method by which a doctor or other medical professional can easily calculate the blood gas data without the need for an arterial blood sample or specialized machines. The present method is intended to be a simple way of quickly and easily testing the patient's blood as a preliminary way to possibly rule out certain conditions. In the event that the results produced by the present method indicate a likelihood of a more serious medical condition, further testing can be ordered including, but not limited to, traditional blood gas testing that uses an arterial blood sample.

In a further embodiment of the present invention, a hand-held calculator is programmed with the mathematical formulas as described herein. A doctor or other medical professional can simply input the pH and [HCO₃—] values into the calculator, or utilize a suitable computer program, to determine the [H+] concentration and the partial pressure of carbon dioxide of the blood sample; a pulse oximeter can further provide the doctor with the oxygen saturation level of the arterial blood.

The present method has several advantages over the standard blood gas test method. Namely, the present method is less expensive since it does not require the use of special machines to analyze a blood sample to give the gas levels of the arterial blood. Further, the present method is less painful to the patient because the needle is inserted into a vein, not an artery. The present method is safer, since accessing blood from a vein is less prone to complications than procedures wherein blood is accessed from an artery. Still further, the present method is faster, since procedures for locating a vein and accessing blood therefrom are less complex and more readily effected than procedures for locating and accessing blood from an artery.

In another aspect of the present invention, the pH level of the venous blood is an especially good indicator of organ dysfunction. A decrease in the pH value of the venous blood may be the first physiological response to dysfunction of one or more organs. Arterial blood flows through an artery to an organ. The blood then passes through the organ and enters the venous blood system. If there is an organ dysfunction (e.g. ischemia), then the venous blood flowing out of such organ may reflect a lower than normal pH value. In one embodiment of the present invention, any changes in venous blood pH levels are able to be correlated with data collected through lab tests in order to locate the particular dysfunctional organ or organs, if any, of the patient. The chart below reveals several such examples:

| Lab Test | Diseased Organ |
|---|---|
| ALT, AST | Liver |
| Alkaline phosphatase | Liver, Bone, Gall Bladder |
| Bilirubin | Liver, Gall Bladder |
| Bun, Creatinine | Kidneys |
| Amylase, Lipase | Pancreas |
| CBC | Blood, Spleen |
| CK | Muscle |
| CKBB | Brain |
| CKMB | Heart |
| CRP | Heart |
| Uric Acid | Joints, Kidneys |
| Rheumatoid Factor | Joints |
| CA125 | Ovary |

Additionally, a doctor can also look for abnormalities on MRI, MRA, and/or cat scan testing in order to locate the particular organ or organs, if any, that are dysfunctional. Preferably, the pH level of the patient's venous blood is monitored by a first device; further, the CMP (complete metabolic profile) of the patient is monitored by a second device. Alternatively, a single device can monitor both the pH level of the patient's venous blood and the CMP of the patient. In accordance with the present invention, a hand-held calculator or computer program then processes this data in order to locate the particular organ or organs, if any, that are dysfunctional; or a doctor can correlate the lab data to locate the particular organ or organs. Additionally, the clinical judgment of the doctor may be used to help identify the dysfunctional organ or organs, if any.

Having thus described the invention in rather full detail, it will be understood that such detail need not be strictly adhered to but that various changes and modifications may suggest themselves to one skilled in the art, all falling within the scope of the present invention as defined by the subjoined claims.

What is claimed is:

1. A method for performing a non-invasive blood gas test on a patient, comprising the steps of:
   a) measuring the pH level of the patient's venous blood;
   b) calculating the level of [H+] concentration (represented in mol per liter) in the patient's venous blood from extrapolating from the following table:

| pH | [H+] in nmol/L |
|---|---|
| 6.8 | 160 |
| 6.9 | 125 |
| 7.0 | 100 |
| 7.1 | 80 |
| 7.2 | 63 |
| 7.3 | 50 |
| 7.4 | 40 |
| 7.5 | 32 |
| 7.6 | 26 |
| 7.7 | 20 |
| 7.8 | 16 | c) measuring the level of serum bicarbonate concentration, [HCO₃—] (in mEq/liter) in the patient's venous blood;
   d) calculating the partial pressure (in mm Hg) of carbon dioxide in the patient's venous blood from the following formula:

$PCO_2 = [H+] \times (1/24) \times [HCO_3-]$; and e) determining the oxygen saturation level (SO$_2$) of the patient's arterial blood by using a pulse oximeter.

2. The method as recited by claim 1, wherein said calculating in steps b) and d), respectively, is performed by a hand-held calculator.

3. The method as recited by claim 1, wherein said calculating in steps b) and d), respectively, is performed by a computer program.

4. A method for performing a non-invasive blood gas test on a patient, comprising the steps of:
   a) measuring the pH level of the patient's venous blood;
   b) calculating the level of [H+] concentration (represented in mol per liter) in the patient's venous blood from the following formulas:

$$pH = -\log_{10}[H+]$$

$$[H+] = \text{Antilog}_{10}(-pH)$$

c) measuring the level of serum bicarbonate concentration, [HCO$_3$—] (in mEq/liter) in the patient's venous blood;
   d) calculating the partial pressure (in mm Hg) of carbon dioxide in the patient's venous blood from the following formula:

$$PCO_2 = [H+] \times (1/24) \times [HCO_3-],$$

wherein [H+] is represented in nmol/L; and
   e) determining the oxygen saturation level (SO$_2$) of the patient's arterial blood by using a pulse oximeter.

5. The method as recited by claim 4, wherein said calculating in steps b) and d), respectively, is performed by a hand-held calculator.

6. The method as recited by claim 4, wherein said calculating in steps b) and d), respectively, is performed by a computer program.

* * * * *